United States Patent
Wang

(10) Patent No.: US 7,402,703 B2
(45) Date of Patent: Jul. 22, 2008

(54) STEREOSELECTIVE SYNTHESIS OF (E)-VINYLBORONIC ESTERS VIA A ZR MEDIATED HYDROBORATION OF ALKYNES

(75) Inventor: Yanong Daniel Wang, Warren, NJ (US)

(73) Assignee: Wyeth, Madison, NJ (US)

( * ) Notice: Subject to any disclaimer, the term of this patent is extended or adjusted under 35 U.S.C. 154(b) by 18 days.

(21) Appl. No.: 11/447,486

(22) Filed: Jun. 6, 2006

(65) Prior Publication Data

US 2006/0281943 A1    Dec. 14, 2006

Related U.S. Application Data

(60) Provisional application No. 60/688,539, filed on Jun. 8, 2005.

(51) Int. Cl.
C07F 5/02    (2006.01)
C07F 5/04    (2006.01)

(52) U.S. Cl. ............................................. 568/1

(58) Field of Classification Search ................ 558/286, 558/287, 288
See application file for complete search history.

(56) References Cited

U.S. PATENT DOCUMENTS 6,680,401 B1 *    1/2004    Marcuccio et al. .......... 558/288

FOREIGN PATENT DOCUMENTS

WO    WO 00/27853 A1    5/2000

OTHER PUBLICATIONS

Schubert Pereira and Morris Srebnik Hydroboration of Alkynes with Pinacolborane Catalyzed by HZrCp2CI. Organometallics 1995, 14,3127-3128.*

Wang et al.: "Zr-Mediated hydroboration: stereoselective synthesis of vinyl boronic esters" Tetrahedron Letters, Elsevier, Amsterdam, NL, vol. 46, No. 50, Dec. 12, 2005, pp. 8777-8780, XP005161806.

Beletskaya I. et al: "Hydroborations Catalysed by Transition Metal Complexes" Tetrahedron, Elsevier Science Publishers, Amsterdam, NL, vol. 53, No. 14, Apr. 7, 1997, pp. 4957-5026, XP004105554, chapter 2.6.5, pp. 4997-4999.

Schubert Pereira et al.: "Hydroboration of Alkynes with Pinacolborane Catalyzed by HZrCp2C1" Organometallics, No. 14, 1995, pp. 3127-3128, XP002402266.

* cited by examiner

*Primary Examiner*—Yvonne Eyler
*Assistant Examiner*—Yevegeny Valenrod
(74) *Attorney, Agent, or Firm*—Stephen E. Johnson

(57) ABSTRACT

There is herein provided a process for Zr-mediated hydroboration of alkynes which offers (E)-vinylboronic esters in high yield with stereoselectivity and regioselectivity.

12 Claims, No Drawings

STEREOSELECTIVE SYNTHESIS OF (E)-VINYLBORONIC ESTERS VIA A ZR MEDIATED HYDROBORATION OF ALKYNES

This application claims priority from provisional application Ser. No. 60/688,539, filed Jun. 8, 2005, the entire disclosure of which is hereby incorporated by reference.

BACKGROUND TO THE INVENTION

This invention relates to a process for Zr-mediated hydroboration of alkynes which offers (E)-vinylboronic esters in high yield with stereoselectivity and regioselectivity.

The formation of new asymmetric carbon-carbon bonds can be readily accomplished using a wide range of palladium-catalyzed cross coupling reactions. One of these processes involves the cross coupling reaction of an organometallic derivative with an alkyl or aryl halide with organoborane.

As one type of frequently used synthetic building block, vinylboronic esters can be prepared by hydroboration of alkynes using catecholborane, under harsh reaction conditions.

Preparation of pinacolborane was reported in 1992 and can be used in place of catecholborane. Pinacolborane has an advantage over catecholborane by providing mild reaction conditions, high functional group tolerance and excellent stability.

The transition metal complex catalyzed hydroboration of alkynes includes development of new methodologies and mechanistic studies. Schwartz Reagent ($Cp_2ZrHCl$) has been used to catalyze hydroboration of alkynes with pinacolborane at room temperature. It was found that hydroboration of less reactive alkynes by this method can be sluggish and stereoselectivity towards E-vinylboronic esters is unsatisfactory, especially for oxygen-containing alkynes.

The process of this invention provides a Zr-mediated hydroboration which offers (E)-vinylboronic esters in high yield and excellent stereoselectivity and regioselectivity.

BRIEF SUMMARY OF THE INVENTION

This invention provides a process for a Zr-mediated hydroboration of alkynes comprising:

reacting a substituted terminal alkyne of formula (I) with a compound of formula II:

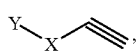

Without a solvent or in an inert solvent in the presence of bis(cyclopentadienyl)zirconium chloride hydride and an amine at temperatures of about 20-150° C., to obtain a compound of formula (III):

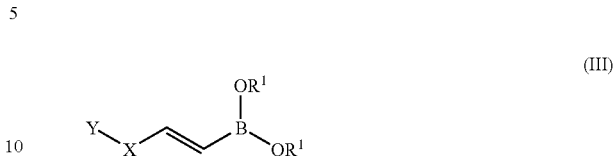

wherein:

X is a divalent group comprising an alkyl, an aryl or a heteroaryl;

$R^1$ is an alkyl, wherein two $R^1$ groups can optionally form a 5-12 membered mono-cyclic or bicyclic ring;

Y is a H, an alkyl, an alkenyl, an aryl or heteroaryl, halogen, CN, $NH_2$, $CO_2H$, $N_3$, CHO, $CF_3$, $OCF_3$, $OR^2$, $OSi(R^2)_3$, $S(O)_mR^2$, $OS(O)_mR^2$, Q, $OR^3Q$, $NR^2S(O)_mR^2$, $OR^3OR^2$, wherein $R^3$ and $R^2$ together may optionally form a heterocyclic ring, $OR^2Q$, $N(R^2)R^3OR^2$, $N(R^2)R^3Q$, $NR^2C(O)R^2$, $C(O)R^2$, $C(O)OR^2$, $C(O)Q$, $OC(O)R^2$, $OC(O)Q$, $NR^2C(O)R^2$, $NR^2C(O)OR^2$, $NR^2C(O)Q$;

m=0-2;

$R^2$ is a H, an alkyl, an alkenyl, or an aryl optionally substituted by an alkyl;

$R^3$ is a divalent alkyl, or an alkenyl;

Q is NZZ' or N(O)ZZ';

Z and Z' may be the same or different group comprising, a H, an alkyl, an alkenyl, an aryl or heteroaryl, wherein Z and Z' taken together with the nitrogen to which they are attached may form a heterocyclic ring.

In one embodiment the solvent used in this invention is dichloromethane, ether, hexanes, toluene, 1,2-dimethoxyethane, and DMF. In another embodiment no solvent is present in the process.

In one embodiment the amine used in this invention is triethylamine, diisopropylethylamine, 4-dimethylaminopyridine, or pyridine and is present in a catalytic amount.

In another embodiment of this invention the reaction temperature is 60° C.

In one embodiment of the invention the bis(cyclopentadienyl)zirconium chloride hydride is present in about 1-100% mole and the amine is present in about 1-100% mole. In another embodiment the bis(cyclopentadienyl)zirconium chloride hydride and amine are present in about 10% mole.

In a further embodiment of the invention the compound of formula (I) is an oxygen containing alkyne.

The following experimental details are set forth to aid in an understanding of the invention, and are not intended, and should not be construed to limit in any way the invention set forth in the claims that follow thereafter.

DETAILED DESCRIPTION OF THE INVENTION

Scheme 1

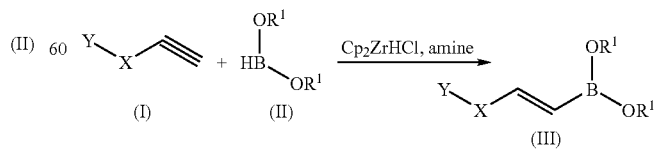

Compounds of formula III can be prepared by a synthetic route depicted in Scheme 1, by reaction of a substituted terminal alkyne (I) with borane $HB(OR^1)_2$ (II) without solvent or in an inert solvent in the presence of about 1-100% mole of bis(cyclopentadienyl)zirconium chloride hydride and about 1-100% mole of an amine at temperatures of about 20-150° C.

In Scheme 1:

X is a divalent group comprising an alkyl, an aryl or a heteroaryl;

$R^1$ is an alkyl, wherein two $R^1$ groups can optionally form a 5-12 membered mono-cyclic or bicyclic ring;

Y is a H, an alkyl, an alkenyl, an aryl or heteroaryl, halogen, CN, $NH_2$, $CO_2H$, $N_3$, CHO, $CF_3$, $OCF_3$, $OR^2$, $OSi(R^2)_3$, $S(O)_mR^2$, $OS(O)_mR^2$, Q, $OR^3Q$, $NR^2S(O)_mR^2$, $OR^3OR^2$, wherein $R^3$ and $R^2$ together may optionally form a heterocyclic ring, $OR^2Q$, $N(R^2)R^3OR^2$, $N(R^2)R_3Q$, $NR^2C(O)R^2$, $C(O)R^2$, $C(O)OR^2$, $C(O)Q$, $OC(O)R^2$, $OC(O)Q$, $NR^2C(O)R^2$, $NR^2C(O)OR^2$, $NR^2C(O)Q$;

m=0-2;

$R^2$ is a H, an alkyl, an alkenyl, or an aryl optionally substituted by an alkyl;

$R^3$ is a divalent alkyl, or an alkenyl;

Q is NZZ' or N(O)ZZ';

Z and Z' may be the same or different group comprising, a H, an alkyl, an alkenyl, an aryl or heteroaryl, wherein Z and Z' taken together with the nitrogen to which they are attached may form a heterocyclic ring.

The outcome of hydroboration using triethylamine improves the stereoselectivity considerably. A catalytic amount of the triethylamine worked better than a stoichiometric amount on both yield and stereoselectivity.

Hydroboration at an elevated temperature affords better stereoselectivity and yield than ambient temperature.

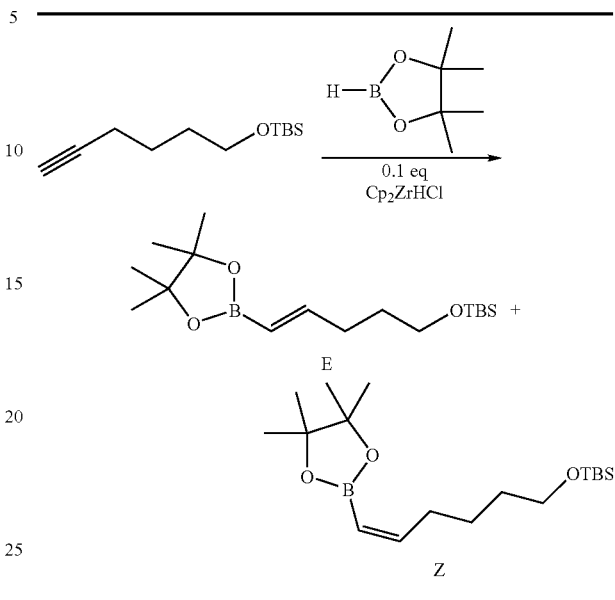

| n | Rxn Time (hr) | Rxn Temp. | Yield (%) | E | Z |
|---|---|---|---|---|---|
| 4 | 20 | rt | 66 | 62 | 38 |
| 4 | 16 | 60° C. | 94 | 96 | 4 |
| 2 | 20 | rt | 62 | 90 | 10 |
| 2 | 16 | 60° C. | 93 | 95 | 5 |

Hydroboration at an elevated temperature in the presence of a catalytic amount of triethylamine resulted in an optimal outcome in both stereoselectivity and yield.

| Additive | Rxn Time (hr) | Rxn Temp. | Yield (%) | E | Z |
|---|---|---|---|---|---|
| none | 20 | rt | 66 | 62 | 38 |
| 1.0 eq $BF_3$—$Et_2O$ | 20 | rt | <5 | 74 | 26 |
| 1.0 eq $Et_3N$ | 20 | rt | 19 | 82 | 18 |
| 0.1 eq pyridine | 20 | rt | 45 | 54 | 46 |
| 0.1 eq DMAP | 20 | rt | 10 | 79 | 21 |
| 0.1 eq $Et_3N$ | 20 | rt | 41 | 93 | 7 |

| Additive | n | Rxn Time (hr) | Rxn Temp. | Yield (%) | E | Z |
|---|---|---|---|---|---|---|
| none | 4 | 20 | rt | 66 | 62 | 38 |
| 0.1 eq $Et_3N$ | 4 | 16 | 60° C. | 94 | 98 | 2 |
| none | 2 | 20 | rt | 62 | 90 | 10 |
| 0.1 eq $Et_3N$ | 2 | 16 | 60° C. | 96 | 98 | 2 |

The terms used in this specification generally have their ordinary meanings in the art, within the context of the invention, and in the specific context where each term is used. Certain terms are discussed below, or elsewhere in the specification, to provide additional guidance to the practitioner in describing the compounds, compositions, and methods of the invention and how to make and use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. The use of examples anywhere in this specification, including examples of any terms discussed herein, is illustrative only, and in no way limits the scope and meaning of the invention or of any exemplified term. Likewise, the invention is not limited to the examples presented.

As used herein, "about" shall generally mean within 20 percent of a given value or range.

The term "alkenyl" refers to unsaturated aliphatic groups which contain at least one double or triple carbon-carbon bond, respectively. The group can be both straight and branched carbon chains of 2-6 carbon atoms in all possible configurational isomers, for example cis and trans. Substitutions can be made to alkenyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6-, 7-,10-, and 14-membered single ring or fused multiple rings aromatic groups, and includes phenyl and napthyl. The aromatic ring can be optionally independently mono-, di-, tri- or tetra-substituted. Substituents are selected from the group consisting of, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moietiesand —CN. The term "aryl" also includes polycyclic ring systems having two or more rings in which two or more carbons are common to two adjoining rings (the rings are "fused") wherein at least one of the carbocyclic rings is aromatic, e.g., the other rings can be cycloalkyls, cycloalkenyls, cycloalkynyls, and/or aryls.

For purposes of this invention an amine is a nitrogen containing chemical species or molecular entity having 1-3 alkyl or aryl groups. In a preferred embodiment a base includes triethylamine, diisopropylethylamine, 4-dimethylaminopyridine, or pyridine.

The term "alkyl" refers to the radical of saturated aliphatic groups of 1-12 carbons, including straight-chain alkyl groups, branched-chain alkyl groups, cycloalkyl (alicyclic) groups, alkyl substituted cycloalkyl groups, and cycloalkyl substituted alkyl groups. In an embodiment, a straight chain or branched chain alkyl has 6 or fewer carbon atoms in its backbone. The term "alkyl" can be used alone or as part of a chemical name as in for example, "trialkylorthoformate". The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. Moreover, the term "alkyl" as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF, —CN and the like.

The term "halogen" refers to an atom of fluorine, chlorine, bromine, or iodine.

The term "heteroaryl" refers to a 4 to 10 membered ring structure in which at least one ring may have an aromatic character and contains 1 to 4 heteroatoms the same or different. The remaining rings of the ring system may be fully unsaturated, partially saturated, or fully saturated. Preferred heteroaryl groups are thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, pteridine, carbazole, phenanthridine, acridine, perimidine, phenanthroline, phenazine, phenothiazine, furazan, phenoxazineand pyrrolidine. The heteroaryl can be independently substituted at one or more positions. Preferred substituents are halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, acyl, aldehyde, ester, a cycloheteroalkyl, an aromatic or heteroaromatic moiety, —CN, or Y'. When the heteroaryl is substituted with Y', Y' is —NH, —O—, —S—, or —NR—, wherein R is an alkyl of 1-6 carbon atoms, at one position on the ring there is further substitution on the —NH, —O—, —S—, or —NR— with a $(CH_2)n$-X' group. For purposes of this invention n is 0-1 and "X'" is cycloalkyl of 3 to 7 carbon atoms, which may be optionally substituted with one or more alkyl of 1 to 6 carbon atoms; or is a pyridinyl, pyrimidinyl, or phenyl ring; wherein the pyridinyl, pyrimidinyl, or phenyl ring may be optionally mono- di-, or tri-substituted with substituents independently selected from the group consisting of halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms, benzoylamino, and —Q—$(CH_2)_m$Ar, wherein Q is selected from O, NH, N($C_1$-$C_6$ alkyl) or S, m is 0, 1 or 2, and Ar is phenyl or pyridyl optionally substituted with one to three moieties independently selected from halogen, alkyl of 1-6 carbon atoms, alkenyl of 2-6 carbon atoms, alkynyl of 2-6 carbon atoms, azido, hydroxyalkyl of 1-6 carbon atoms, halomethyl, alkoxymethyl of 2-7 carbon atoms, alkanoyloxymethyl of 2-7 carbon atoms, alkoxy of 1-6 carbon atoms, alkylthio of 1-6 carbon atoms, hydroxy, trifluoromethyl, cyano, nitro, carboxy, carboalkoxy of 2-7 carbon atoms, carboalkyl of 2-7 carbon atoms, phenoxy, phenyl, thiophenoxy, benzoyl, benzyl, amino, alkylamino of 1-6 carbon atoms, dialkylamino of 2 to 12 carbon atoms, phenylamino, benzylamino, alkanoylamino of 1-6 carbon atoms, alkenoylamino of 3-8 carbon atoms, alkynoylamino of 3-8 carbon atoms and benzoylamino. The heteroaryl may be oxidized on a nitrogen atom to provide the corresponding N-oxide, such as pyridine-N-oxide or quinoline -N-oxide. The heteroaryl may also be oxidized on a tri-substituted nitrogen atom to provide the corresponding N-oxide, such as N-ethylpiperazine-N-oxide. In another embodiment the heteroaryl may contain a carbonyl group on one of the carbon atoms, such as pyrrolidinone, 1,3,4-oxadiazol-2-one, or 2-indanone.

The term "heteroatom" as used herein means an atom of any element other than carbon or hydrogen and include for example nitrogen, oxygen, sulfur, phosporus, and selenium.

For purposes of this invention a solvent is the term applied to the whole initial liquid phase containing the extractant. The solvent may contain only one extractant or it may be a composite homogeneous mixture of extractant(s) with diluent(s).

For purposes of this invention an inert solvent the solvent as previously defined does not react with any of the compounds of scheme 1 and includes but is not limited to dichloromethane, ether, hexanes, toluene, 1,2-dimethoxyethane, or DMF.

For the purposes of this invention the term "substituted" refers to where a hydrogen radical on a molecule has been replaced by another atom radical, a functional group radical or a moiety radical; these radicals being generally referred to as "substituents."

In order to facilitate a further understanding of the invention, the following non-limiting examples illustrate the process of the present invention.

EXAMPLE 1

2-[6-(tert-Butyl-dimethyl-silanyloxy)-hex-1-enyl]-4,4,5,5-tetramethyl-[1,3,2]dioxaborolane

MS (M+H) 341.3

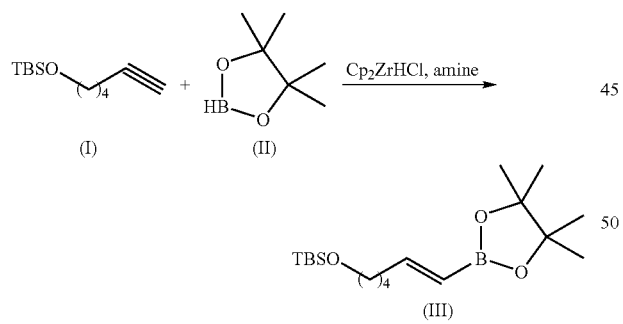

To a mixture of tert-butyl-but-3-ynyloxy-dimethyl-silane (I) (1.0 g, 7.14 mmol) and 4,4,5,5-tetramethyl-[1,3,2]dioxaborolane (II) (958 mg, 7.49 mmol) were added bis(cyclopentadienyl)zirconium chloride hydride (183 mg, 0.714 mmol) and triethylamine (72 mg, 0.714 mmol). The resulting mixture was heated at 60° C. for 6 hours and was diluted with hexanes. The precipitate was removed by filtering over a short pad of silica gel and washed with hexanes. The filtrate was concentrated and dried through vacuum to give 1.76 g (93%) of the title compound as a colorless liquid.

The following examples (2- were prepared according to the procedures of example 1 above.

EXAMPLE 2

2-{[(3E)-4-(4,4,5,5-Tetramethyl-1,3,2-dioxaborolan-2-yl)but-3-enyl]oxy}tetrahydro-2H-pyran The title compound was prepared from 2-but-3-ynyloxy-tetrahydro-pyran. MS (M+H) 282.2.

EXAMPLE 3 tert-Butyl(dimethyl){[(3E)-4-(4,4,5,5-tetramethyl-1,3,2-dioxaborolan-2-yl)but-3-en-1-yl]oxy}silane The title compound was prepared from tert-butyl-but-3-ynyloxy-dimethyl-silane. MS (M+H) 313.2.

EXAMPLE 4

2-[(1E)-Hex-1-en-1-yl]-4,4,5,5-tetramethyl-1,3,2-dioxaborolane

The title compound was prepared from 1-hexyne. MS (M+H) 252.2

EXAMPLE 5

2-[(E)-2-Cyclohexylvinyl]-4,4,5,5-tetramethyl-1,3,2-dioxaborolane

The title compound was prepared from cyclohexyl acetylene. MS (M+H) 278.2

EXAMPLE 6

4,4,5,5-Tetramethyl-2-[(E)-2-phenylvinyl]-1,3,2-dioxaborolane

The title compound was prepared from phenyl acetylene. MS (M+H) 272.1

EXAMPLE 7 tert-Butyl(dimethyl){[(4E)-5-(4,4,5,5-tetramethyl-1,3,2-dioxaborolan-2-yl)pent-4-en-1-yl]oxy}silane The title compound was prepared from tert-butyl-dimethyl-pent-4-ynyloxy-silane. MS (M+H) 327.3

EXAMPLE 8

(5E)-6-(4,4,5,5-Tetramethyl-1,3,2-dioxaborolan-2-yl)hex-5-en-1-yl acetate

The title compound was prepared from 3-butynyl-1-acetate. MS (M+H) 269.3

EXAMPLE 9

2-[(1E)-3-(Ethylthio)prop-1-en-1-yl]-4,4,5,5-tetramethyl-1,3,2-dioxaborolane

The title compound was prepared from 3-ethylsulfanyl-propyne. MS (M+H) 228.1

EXAMPLE 10

2-[(E)-2-(3-Methoxyphenyl)vinyl]-4,4,5,5-tetramethyl-1,3,2-dioxaborolane

The title compound was prepared from 3-ethynylanisole. MS (M+H) 261.1

EXAMPLE 11

(5E)-6-(4,4,5,5-Tetramethyl-1,3,2-dioxaborolan-2-yl)hex-5-enenitrile

The title compound was prepared from 5-hexynenitrile. MS (M+H) 221.2

EXAMPLE 12

(3E)-4-(4,4,5,5-Tetramethyl-1,3,2-dioxaborolan-2-yl)but-3-en-1-yl 4-methylbenzene-sulfonate The title compound was prepared from 3-butynyl p-toluenesulfonate. MS (M+H) 370.2

EXAMPLE 13 tert-Butyl(dimethyl){[(2E)-1-methyl-3-(4,4,5,5-tetramethyl-1,3,2-dioxaborolan-2-yl)prop-2-en-1-yl]oxy}silane The title compound was prepared from tert-butyl-dimethyl-(1-methyl-prop-2-ynyloxy)-silane. MS (M+H) 313.3

What is claimed:

1. A process for a Zr-mediated hydroboration of alkynes comprising:

reacting a substituted terminal alkyne of formula (I) with a compound of formula II:

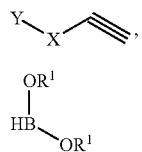

Without a solvent or in an inert solvent in the presence of bis(cyclopentadienyl)zirconium chloride hydride and an amine at temperatures of about 20-150° C., to obtain a compound of formula (III):

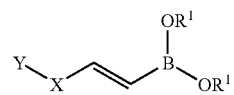

wherein:

X is a divalent group comprising an alkyl, an aryl or a heteroaryl;

$R^1$ is an alkyl, wherein two $R^1$ groups can optionally form a 5-12 membered mono-cyclic or bicyclic ring;

Y is a H, an alkyl, an alkenyl, an aryl or heteroaryl, halogen, CN, $NH_2$, $CO_2H$, $N_3$, CHO, $CF_3$, $OCF_3$, $OR^2$, $OSi(R^2)_3$, $S(O)_mR^2$, $OS(O)_mR^2$, Q, $OR^3Q$, $NR^2S(O)_mR^2$, $OR^3OR^2$, wherein $R^3$ and $R^2$ together may optionally form a heterocyclic ring, $OR^2Q$, $N(R^2)R^3OR^2$, $N(R^2)R^3Q$, $NR^2C(O)R^2$, $C(O)R^2$, $C(O)OR^2$, $C(O)Q$, $OC(O)R^2$, $OC(O)Q$, $NR^2C(O)R^2$, $NR^2C(O)OR^2$, $NR^2C(O)Q$;

m=0-2;

$R^2$ is a H, an alkyl, an alkenyl, or an aryl optionally substituted by an alkyl;

$R^3$ is a divalent alkyl, or an alkenyl;

Q is NZZ' or N(O)ZZ';

Z and Z' may be the same or different group comprising, a H, an alkyl, an alkenyl, an aryl or heteroaryl, wherein Z and Z' taken together with the nitrogen to which they are attached may form a heterocyclic ring.

2. The process of claim 1 wherein the solvent is dichloromethane, ether, hexanes, toluene, 1,2-dimethoxyethane, and DMF.

3. The process of claim 1 wherein no solvent is present.

4. The process of claim 1 wherein the amine is triethylamine, diisopropylethylamine, 4-dimethylaminopyridine, or pyridine.

5. The process of claim 4 wherein the amine is triethylamine.

6. The process of claim 4 wherein the amine is present in a catalytic amount.

7. The process of claim 1 wherein temperature is 60° C.

8. The process of claim 1 wherein the bis(cyclopentadienyl)zirconium chloride hydride is present in about 1-100% mole.

9. The process of claim 8 wherein the bis(cyclopentadienyl)zirconium chloride hydride is present in about 10% mole.

10. The process of claim 1 wherein the amine is present in about 1-100% mole.

11. The process of claim 10 wherein the amine is present in about 10% mole.

12. The process of claim 1 wherein the compound of formula (I) is an oxygen containing alkyne.

* * * * *